(12) United States Patent
Johnsen et al.

(10) Patent No.: US 6,822,736 B2
(45) Date of Patent: Nov. 23, 2004

(54) METHOD AND SYSTEM FOR AUTOMATIC ANALYSIS OF PARTICLES

(75) Inventors: Ole Magne Johnsen, Skien (NO); Terje Jørgensen, Skien (NO); Frode Reinholt, Skien (NO)

(73) Assignee: Norsk Hydro ASA, Oslo (NO)

( * ) Notice: Subject to any disclaimer, the term of this patent is extended or adjusted under 35 U.S.C. 154(b) by 0 days.

(21) Appl. No.: 10/258,750

(22) PCT Filed: Apr. 23, 2001

(86) PCT No.: PCT/NO01/00169

§ 371 (c)(1),
(2), (4) Date: Mar. 6, 2003

(87) PCT Pub. No.: WO01/84115

PCT Pub. Date: Nov. 8, 2001

(65) Prior Publication Data

US 2003/0156285 A1 Aug. 21, 2003

(30) Foreign Application Priority Data

Apr. 28, 2000 (NO) .......................................... 20002227

(51) Int. Cl.$^7$ ............................................. G01N 15/02
(52) U.S. Cl. ...................................................... 356/335
(58) Field of Search ................................ 356/335–343, 356/73, 383, 384, 36; 250/573–577

(56) References Cited

U.S. PATENT DOCUMENTS 5,532,942 A   7/1996   Kitamura et al.
5,786,894 A   7/1998   Shields
6,010,593 A   1/2000   Eymin Petot Tourtollet et al.

FOREIGN PATENT DOCUMENTS

| JP | 11-258141 | 9/1999 |
| WO | 90/12310 | 10/1990 |
| WO | 99/15877 | 4/1999 |

*Primary Examiner*—Michael P. Stafira

(74) *Attorney, Agent, or Firm*—Wenderoth Lind & Ponack, L.L.P.

(57) ABSTRACT

In a method and a system for automatic analysis of particle size distribution, shape and color, sampled particles are distributed into a substantially monolayer particle stream to be exposed to a light source for providing imaging and subsequent analysis of the particles. The samples are collected manually or automatically and placed in containers provided with identification codes which can be read/typed manually or automatically, recorded optically or electronically and the containers are placed in storage devices or sample magazines which can be connected to a sample distribution device for forming the particle stream. The samples can be collected from various process streams and the containers for these samples can be placed in the same storage device for being analyzed as a series of analyses. The imaging of the particle stream is performed by a camera chosen among several cameras present in the analyzing device according to the particle size distribution of the sample.

17 Claims, 3 Drawing Sheets

METHOD AND SYSTEM FOR AUTOMATIC ANALYSIS OF PARTICLES

FIELD OF THE INVENTION

The present invention relates to a method for automatic analysis to determine particle size distribution, shape and color, and an apparatus for performing the method. The method includes a collection of particle samples, and a transportation of the collected particle samples to a means for distributing the particles into a particle stream. The means for distributing the particles forms a curtain where the particles are substantially distributed in a monolayer to be exposed to a light source for providing an image of the particle curtain to be analyzed. The apparatus comprises sample collecting devices, and a transport means for transporting the samples to a device for distribution of the samples into a particle stream suitable for imaging and subsequent analysis.

BACKGROUND OF THE INVENTION

The main problem experienced in particle analysis is that commercially available apparatuses and methods only solve separate tasks within the field. Several manual operations are necessary for carrying out the total analysis process, and accordingly, only part of the process will in practice be automatic. In most cases, only separate samples can be analyzed at any given time, and new samples have to be collected, prepared, marked/registered and formed into suitable particle streams for imaging and subsequent computerized analysis/treatment of the images. The result of these problems is that it is quite time-consuming to perform analysis of particle samples, as well as a series of samples from different production streams of a plant.

Several apparatuses and measuring/analyzing techniques related to particle analysis are known in the art. For example, a particle analysis apparatus where a silhouette projection method is used is described in U.S. Pat. No. 4,497,576. The apparatus includes use of parallel laser beams directed through a sample of particles, and a means for recording the light which has passed through. This recording is then analyzed to reveal the particle size distribution of the sample. The particles to be analyzed are transported on a conveyor belt and fall from it in front of a light source and down to a next belt to be returned to the process. The particles falling from the belt form a monolayer of particles and they fall at the same speed. How this can be achieved is not explained.

Analysis of particle size distribution is also known from EP-0348469 B1, which describes a method and means for creating a monolayer curtain of particles to be analyzed. The particles are fed manually via a silo onto a vibrating plate disposed at such a distance from the silo outlet that the uppermost layer of said particles on said plate forms an angle with the horizontal plane which is 95%–50% of the sliding angle of said particles. Though a reliable monolayer is provided with this method and means, they are restricted to analyzing single samples, one at a time. The imaging of the particle curtain has to be finalized before a new sample of particles can be fed to the apparatus for being formed into a monolayer of particles.

Imaging and analyzing of a particle stream is also known from GB-2,333,594 A, which describes an apparatus comprising electro-optical scanning of the particle stream with an optoelectronic measurement section formed by a light source and an image collecting device. The image collecting device comprises a plurality of electro-optical image recording units aligned onto the particle stream, said units having different image scales which are mutually matched to cover the overall measurement range of the apparatus. This way of covering the overall measurement range avoids the manual work of changing lenses and camera position, but it is also restricted to performing analysis of single samples, and there are no special provisions for securing a monolayer of particles to be imaged.

In U.S. Pat. No. 4,295,200 there is described an automatic particle analyzing system comprising a supply of several samples to a particle distributor. Sample cups filled with particles are fixed on to a conveyer belt which can pass over a particle distribution device. A measured stream of particles is dropped onto the apex of a distribution cone when a cup passes over the cone. The particles are then divided into a circular pattern falling through a narrow sizing zone onto the spherical edge of a rotatable platen. By this means, the particles can be analyzed one-by-one as each particle is carried into a frame area and viewed, preferably by a microscope and a TV camera, the output of which is applied to a computer programmed to analyze selected characteristics. This system makes it possible to analyze each particle in a sample, and can continue on to the next sample when the last particle of the first sample is analyzed. But such a device is very sensitive to the particle size distribution before imaging, as large particles will get stuck in the narrow sizing zone of the apparatus. Another limitation of the capacity of the system is that the particles have to be analyzed one-by-one, and the practical use of this system will be restricted to laboratories as it is not applicable for analyzing particles in a continuous industrial process.

SUMMARY OF THE INVENTION

The main object of the present invention is to arrive at a versatile and automatic method and apparatus for the analysis of a plurality of samples of particles and being applicable both for on-line analysis and laboratory analysis.

Another object is to combine sample collections from various process streams with supply of these to a single particle analyzing apparatus without applying any manual work and still being able to keep track of the origin of the samples with regard to a time and place for collection of the various samples.

A further object is to be able to perform sequential analysis of samples, for instance, analysis of samples taken at the same time from various process streams.

It is also an object to develop a method that can cover a wide range of particle size distribution, shape and color.

In spite of the fact that numerous methods and apparatuses for particle analysis are on the market, the inventors of the present invention have found that none of these, or combinations thereof, could meet their demand for a versatile and robust system. A thorough investigation of advantages and disadvantages of known methods revealed that further developments were necessary for reducing the manual work in connection with particle analysis. It was also found that quality control of such systems needed to be improved. The inventors first looked into each manual operation in order to evaluate the possibility for automation and improvement of the operation. It was found that the sampling should be combined with placement of the sampled particles in containers which could be transported to the central unit of a particle analyzer. This conclusion led to the problem of identifying the samples later on. This problem is simply solved by providing each container with identification codes (ID) which can be arranged in sample sequence in the magazine, wherein the analyzer is set up for analyzing the samples according to the sequence of the samples and/or read for recording by conventional optical/electronic registration devices. It is then possible to identify the samples throughout the whole process with regard to a time and place for the sampling and also other information of interest such as temperature, humidity etc. at the time of sampling. In some cases it is of interest to treat the samples before analyses. Such treatment, comprising drying, dividing, crushing, sieving etc., should be performed before the sample is put into the container. In connection with particle analysis, it would in some cases be an advantage if the analysis could be performed in sequences or series, for instance, performing analysis in series of samples taken at the same time from different process streams. The inventors found that this could be achieved by applying the concept of sample containers having ID's. Desired sample series can be collected into one storage device supplied to the central analyzing apparatus. In other cases, several samples from one sample collection site can be stored in said storage device for transport to the analyzer. By the above arrangement, any desired series of samples can be fed to the analyzer, where separate samples from the storage device can be transformed into a stream of particles having a suitable form for being imaged and analyzed. The particle stream preferably constitutes a monolayer of particles, and this can be achieved by known means such as vibrating plates to which the sample is fed. Further, it was found that even the imaging part could be improved by providing several image recording devices such as cameras in the analyzer. The cameras could have different size/type of lenses, and depending on the type of samples and size of particles to be analyzed, the appropriate camera or cameras can be put into operation. As the system comprises computer programs for an automatic selection of the camera or cameras and for automatic collection of samples, and even placement of these into desired storage compartments, the results from the analyzer can be used to trigger samples and types of samples to be analyzed next. The analysis can of course also be used as feedback to a process. The system is advantageously equipped with various types of alarms which are triggered when the analysis shows predetermined deviations from desired values.

The main feature of the method according to the present invention is that the samples are collected manually or automatically and placed in containers provided, as known per se, with identification codes which can be read/typed manually or automatically, recorded optically or electronically, wherein the containers are placed in storage devices or sample magazines which can be connected to a sample distribution device for forming a particle stream suitable for imaging and subsequent analysis, and wherein the imaging of the particle stream is performed by a camera chosen among several cameras present in the analyzing device according to the particle size distribution of the sample.

Prior to placement in containers, the samples can be subjected to treatment like drying, dividing, crushing or sieving.

The samples can be collected from various process streams, and the containers for these samples can be placed in the same storage device for being analyzed as a series of analyses.

The results of the analysis can trigger feedback or an alarm if the results deviate from pre-defined values and said feedback can be conveyed to the control system of the process.

The containers can be provided with samples in a sequence in the magazine, and the analyzer can be set up for analyzing the samples according to the sequence of the samples.

The sample containers can contain samples with a wide range of particle size distributions, shape and color.

The main features of the automatic particle analyzing system according to the invention comprise devices for automatic collection of samples and containers 2 with identification codes for the samples and storage compartments 3 for said containers 2. The samples can be emptied one by one into a sample distribution device 4 for forming particle streams suitable for imaging by a camera, which can be chosen among several cameras present in the analyzing device, and subsequent analysis.

The system can comprise several imaging devices being cameras having different types of lenses which can be put automatically into operation as a function of the size of particles to be analyzed.

The system can comprise several compartments for sample containers and there can be provisions for the transportation of said compartments to the sample distribution device.

DETAILED DESCRIPTION OF THE INVENTION

Figure 1:
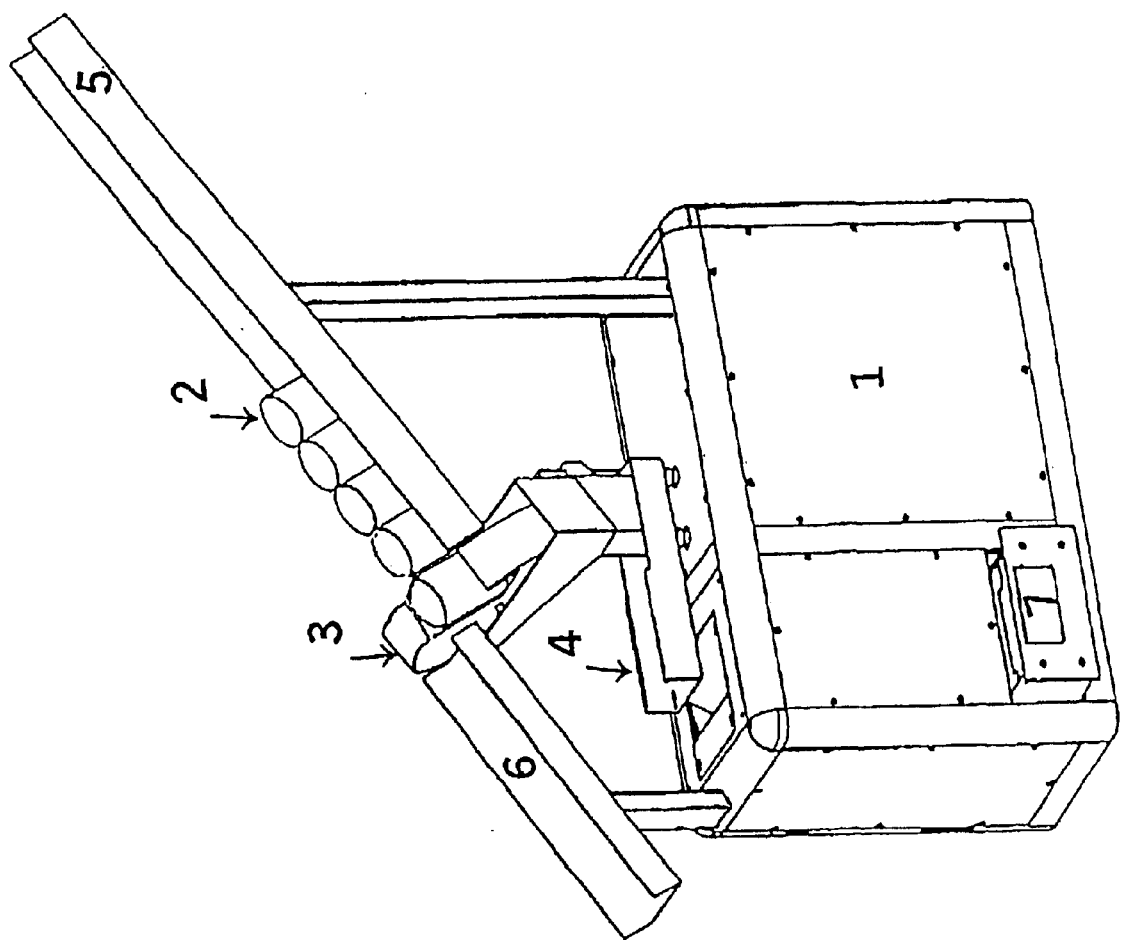
FIG. 1 shows the central units of a particle analysis system according to the present invention.
Figure 2:
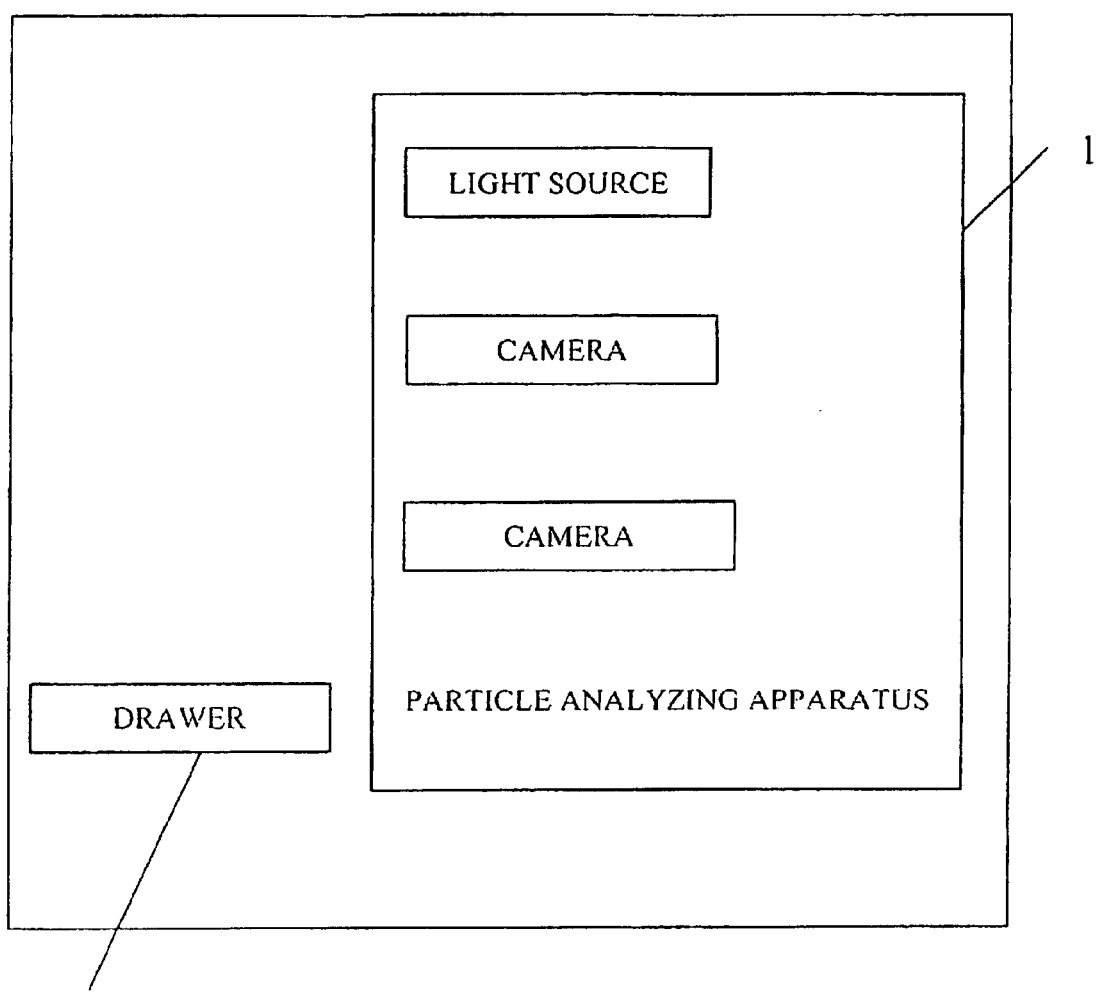
FIG. 2 is a block diagram of the particle analyzing apparatus according to the present invention.

In FIG. 1, there is shown a particle analyzing apparatus 1 comprising imaging devices such as at least one camera and a light source for illuminating the stream of particles delivered from the vibrating chute 4 into the apparatus 1. FIG. 2 is a block diagram showing the light source and a plurality of cameras included within the particle analyzing apparatus 1. After having been analyzed, the particles are collected and removed from the apparatus 1 through the drawer 7. A conveyor belt can also be used for removing the analyzed particles, and if desired, returned to the process from which they were collected. The samples of particles are transported from the sampling site to the central unit in containers 2. These can then be fed to the chute 5 and further into a rotatable storage compartment 3. The containers 2 can also be loaded into compartment 3, which then are connected to the central analyzing unit. When the compartment 3 rotates, the containers 2 are emptied down on a vibrating chute 4. The particles leave the chute 4 in a stream which is substantially a monolayer of particles. Emptied containers 2 leave the central unit through chute 6 and are then transported back to the process for being refilled with samples of particles to be analyzed.

Figure 3:
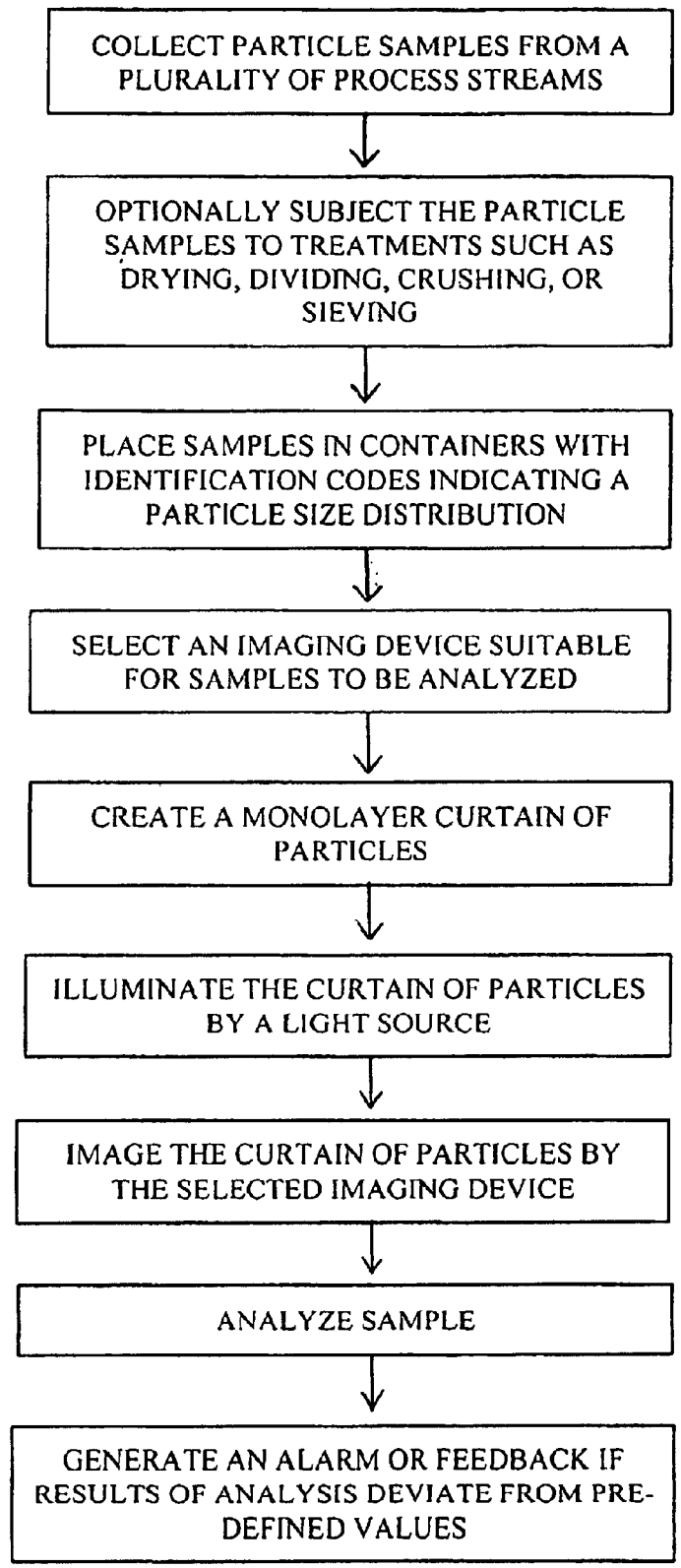
FIG. 3 is a flowchart of a particle analysis method according to the present invention.

By applying the method shown in FIG. 3 and the automatic analyzing system as shown in FIG. 1, the inventors have succeeded in solving the main problems related to known methods and systems in the field. A versatile, robust and high capacity method and system have been achieved by the invention. Manual labor has been minimized and the quality control and reliability of the particle analysis have been substantially increased as a result of applying sample containers with ID's.

What is claimed is:

1. A method for automatic analysis of particle size distribution, shape and color, comprising:

collecting particle samples, wherein each particle sample comprises a plurality of particles;

transporting the particle sample to a sample distribution device operable to distribute each of the particle samples into a substantially monolayer vertical particle stream, wherein each of the substantially monolayer vertical particle streams is exposed to a light source;

wherein the particle samples are collected manually or automatically, and are placed in containers provided with an identification code that is based on the particle sample contained therein, wherein the containers are placed in a storage device or a sample magazine which is connected to the sample distribution device, and wherein, for each particle sample, imaging of the substantially monolayer vertical particle stream is performed by a camera, chosen among several cameras, according to the particle size distribution of the particle sample.

2. The method according to claim 1, wherein the particle samples are subjected to drying, dividing, crashing or sieving, prior to the particle samples being placed in the containers.

3. The method according to claim 1, wherein the particle samples are collected from a plurality of process streams, wherein the containers for the collected particle samples are placed in the same storage device, and wherein the collected particle samples are analyzed in a series of analyses.

4. The method according to claim 1, wherein results of analyzing the collected particle samples triggers feedback or an alarm if the results deviate from pre-defined values, wherein said feedback is conveyed to a control system.

5. The method according to claim 1, wherein the containers provided with particle samples are disposed in a sequence in the storage device or the sample magazine, and wherein the particle samples are analyzed according to the sequence of the particle samples.

6. The method according to claim 1, wherein the containers contain particle samples with a wide range of particle size distributions, shape and color.

7. An automatic particle analyzing system for analyzing a plurality of particle samples, wherein each particle sample comprises a plurality of particles, said system comprising:

a transportation mechanism operable to transport the particle samples to a sample distribution device operable to distribute each of the particle samples into a vertical particle stream suitable for imaging and subsequent analysis;

a plurality of containers operable to hold the particle samples therein;

a collection mechanism operable to collect the particle samples and the containers, wherein each container is provided with an identification code associated with the particle sample contained therein; and a storage compartment for said containers;

wherein the particle samples are emptied one by one from the storage compartment into the sample distribution device; and wherein, for each particle sample, a camera is chosen, among several cameras, to image the vertical particle stream based on the identification code associated with the particle sample.

8. The system according to claim 7, wherein, for each particle sample, the identification code includes information regarding the particle size distribution of the particle sample within the container.

9. The system according to claim 7, wherein only one camera is chosen for each particle sample.

10. The system according to claim 7, wherein the particles in each vertical particle stream are not immersed in water.

11. The system according to claim 7, wherein the sample distribution device comprises a vibrating chute.

12. The system according to claim 11, wherein the storage compartment comprises a rotatable storage compartment operable to transfer the particle samples from the containers to the vibrating chute.

13. The system according to claim 7, wherein each of the vertical particle streams comprises a substantially single layer vertical particle stream.

14. The method according to claim 1, wherein, for each particle sample, the identification code includes information regarding the particle size distribution of the particle sample within the container.

15. The method according to claim 1, wherein the identification codes can be read manually or automatically, and can be recorded optically or electronically.

16. The method according to claim 1, wherein only one camera is chosen for each particle sample.

17. The method according to claim 1, wherein the particles in each vertical particle stream are not immersed in water.

* * * * *